(12) United States Patent
Buntru et al.

(10) Patent No.: US 11,317,623 B2
(45) Date of Patent: May 3, 2022

(54) CELL-FREE PROTEIN SYNTHESIS SYSTEM

(71) Applicant: Fraunhofer-Gesellschaft zur Foerderung der angewandten Forschung e.V., Munich (DE)

(72) Inventors: Matthias Buntru, Aachen (DE); Simon Vogel, Aachen (DE); Stefan Schillberg, Aachen (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 243 days.

(21) Appl. No.: 16/480,261

(22) PCT Filed: Jan. 25, 2018

(86) PCT No.: PCT/EP2018/051822
§ 371 (c)(1),
(2) Date: Jul. 23, 2019

(87) PCT Pub. No.: WO2018/138195
PCT Pub. Date: Aug. 2, 2018

(65) Prior Publication Data
US 2019/0380330 A1   Dec. 19, 2019

(30) Foreign Application Priority Data

Jan. 25, 2017   (EP) ..................................... 17153005

(51) Int. Cl.
*A01N 3/00*     (2006.01)
*C12N 15/82*    (2006.01)
*C12P 21/02*    (2006.01)

(52) U.S. Cl.
CPC ........... *A01N 3/00* (2013.01); *C12N 15/8257* (2013.01); *C12P 21/02* (2013.01)

(58) Field of Classification Search
None
See application file for complete search history.

(56) References Cited

U.S. PATENT DOCUMENTS

| | | |
|---|---|---|
| 6,168,931 B1 | 1/2001 | Swartz et al. |
| 6,337,191 B1 | 1/2002 | Swartz et al. |
| 2002/0039771 A1 | 4/2002 | Peters et al. |
| 2003/0199076 A1 | 10/2003 | Kuroita et al. |

FOREIGN PATENT DOCUMENTS

| | | |
|---|---|---|
| WO | 2014198760 A1 | 12/2014 |
| WO | 2016/112258 A1 | 7/2016 |

OTHER PUBLICATIONS

Bradford, Marion M. "A Rapid and Sensitive Method for the Quantitation of Microgram Quantities of Protein Utilizing the Principle of Protein-Dye Binding," Analytical Biochemistry, 1976, 72:248-254.
Carlson et al. "Cell-Free Protein Synthesis: Applications Come of Age," Biotechnology Advances, 2012, 30(5):1185-1194.
Goerke et al. "Development of Cell-Free Protein Synthesis Platforms for Disulfide Bonded Proteins," Biotechnology and Bioengineering, Feb. 1, 2008, 99(2)351-367.
Goshima et al. "Human Protein Factory for Converting the Transcriptome into an in Vitro-Expressed Proteome," Nature Methods, Dec. 2008, 5(12):1011-1017.
Gursinsky et al. "Replication of Tomato Bushy Stunt Virus RNA in a Plant in Vitro System," Virology, 2009, 390(2):250-260.
Hodgman et al. "Optimized Extract Preparation Methods and Reaction Conditions for Improved Yeast Cell-Free Protein Synthesis," Biotechnology and Bioengineering, Oct. 2013, 110(10):2643-2654.
Hoffman et al. "Rapid Translation System: A Novel Cell-Free Way from Gene to Protein," 2004, Biotechnology Annual Review, 10:1-30.
Kanter et al. "Cell-Free Production of scFv Fusion Proteins: An Efficient Approach for Personalized Lymphoma Vaccines," Blood, Apr. 15, 2007, 109(8):3393-3399.
Komoda et al. "Replication of Plan RNA Virus Genomes in a Cell-Free Extract of Evacuolated Plant Protoplasts," PNAS, Feb. 17, 2004, 101(7):1863-1867.
Kovtun et al. "Towards the Construction of Expressed Proteomes Using a Leishmania Tarentolae Based Cell-Free Expression System," PlosOne, Dec. 2010, 5(12):e14388.
Kubick et al. "Chapter 2: In Vitro Synthesis of Posttranslationally Modified Membrane Proteins," Current Topics in Membranes, 2009, 63:25-49.
Madin et al. "A Highly Efficient and Robust Cell-Free Protein Synthesis System Prepared from Wheat Embryos: Plants Apparently Contain a Suicide System Directed at Ribosomes," PNAS, Jan. 18, 2000, 97(2):559-564.
Mureev et al. "Species-Independent Translational Leaders Facilitate Cell-Free Expression," Nature Biotechnology, Aug. 2009, 27(8):747-752.
Stech et al. "Production of Functional Antibody Fragments in a Vesicle-Based Eukaryotic Cell-Free Translation System" Journal of Biotechnology, 2012, 164:220-231.
Takai et al. "Practical Cell-Free Protein Synthesis System Using Purified Wheat Embryos," Nature Protocols, 5(2):227-238.
Tarui et al. "Establishment and Characterization of Cell-Free Translation/ Glycosylation in Insect Cell (Spodoptera Frugiperda 21) Extract Prepared with High Pressure Treatment," Applied Microbiology and Biotechnology, 2001, 55:446-453.
Yang et al. "Rapid Expression of Vaccine Proteins for B-Cell Lymphoma in a Cell-Free System," Biotechnology and Bioengineering, Mar. 5, 2005, 89(5): 503-511.
Yin et al. "Aglycosylated Antibodies and Antibody Fragments Produced in a Scalable in Vitro Transcription-Translation System," mAbs, Mar./Apr. 2012, 4(2):217-225.

(Continued)

*Primary Examiner* — Marsha Tsay
(74) *Attorney, Agent, or Firm* — Wagenknecht IP Law Group PC

(57) ABSTRACT

The technology provided herein relates to novel methods and systems for cell-free protein synthesis, in particular to cell-free protein synthesis systems suitable for protein synthesis before and after freezing for a short- or long-term storage, wherein said system comprises a cryoprotectant.

10 Claims, 1 Drawing Sheet

(56) References Cited

OTHER PUBLICATIONS

Tawada et al. "Microscale to Manufacturing Scale-Up of Cell-Free Cytokine Production—A New Approach for Shortening Protein Production Development Timelines," Biotechnology and Bioenginieering, Jul. 2011, 108(7):1570-1578.
PCT/EP2018/051822 International Search Report and Written Opinion dated Mar. 5, 2018.
Sideso Odafe et al. "The Characteristics and Stabilization of a Caffeine Demethylase Enzyme Complex," International Journal of Food Science and Technology, Aug. 1, 2001, 36(6):693-698.
Buntru et al. "A Versatile Coupled Cell-Free Transcription-Translation System Based on Tobacco BY-2 Cell Lysates." Biotechnology and Bioengineering, May 2015, 112(5):867-878.
Buntru et al. "Tobacco BY-2 Cell-Free Lysate: An Alternative and Highly Productive Plant-Based in Vitro Translation System," BMC Biotechnology, May 2014, 14(1)37 p. 1-11.

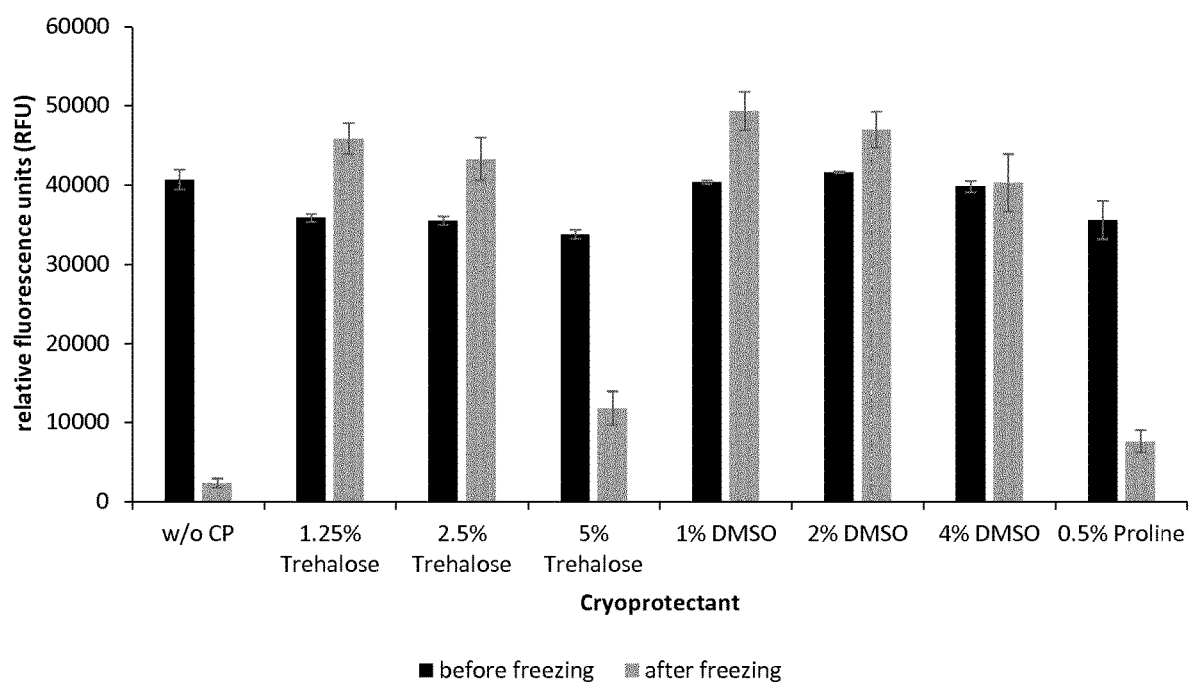

CELL-FREE PROTEIN SYNTHESIS SYSTEM

CROSS REFERENCE TO RELATED APPLICATIONS

This is a US national phase application under 35 USC § 371 of international patent application no. PCT/EP2018/051822, filed Jan. 25, 2018, which itself claims priority to European application 17153005.8, filed Jan. 25, 2017. Each of the applications referred to in this paragraph are herein incorporated by reference in their entireties herein.

FIELD OF THE DISCLOSURE

The present disclosure pertains to novel methods and systems for cell-free protein synthesis, in particular to cell-free protein synthesis systems suitable for protein synthesis before and after freezing for a short- or long-term storage, wherein said system comprises a cryoprotectant.

BACKGROUND

The increasing demand for new therapeutic proteins, technical enzymes, protein engineering and functional genomics requires a rapid and efficient protein production and screening platform.

The emerging technology of cell-free protein synthesis (CFPS) can help to satisfy this demand (Carlson et al., 2012). CFPS systems based on crude lysates provide several advantages over in vivo systems and offer broad applications in protein engineering, biopharmaceutical product development and post-genomic research.

Compared to cell-based expression, CFPS offers advantages such as shorter process times and the direct control and monitoring of reaction conditions. PCR products can be used directly for the simultaneous expression of multiple proteins without laborious cloning and transformation steps. CFPS platforms allow the addition of accessory factors that promote protein folding or the incorporation of unnatural amino acids (Albayrak and Swartz, 2013; White et al., 2013). They also facilitate the expression of cytotoxic proteins that cannot be produced in living cells.

Crude lysates contain the necessary components for translation, protein folding, and energy metabolism, so providing them with amino acids, energy substrates, nucleotides and salts allows almost any protein encoded by a RNA template to be synthesized. In coupled transcription/translation systems supplemented additionally with an appropriate RNA polymerase DNA templates can also be used.

As mentioned above, in contrast to traditional cell-based expression methods, CFPS offers shorter process times, limited protein hydrolysis and the ability to express toxic proteins or proteins containing specific chemical groups or unnatural amino acids at defined positions.

Furthermore, the open nature of the system allows the reaction to be controlled and monitored directly. Although chemical synthesis allows the rapid and controlled synthesis of peptides <40 residues in length, this is not an economically feasible method for the production of larger polypeptides.

The most widely used cell-free systems are based on *Escherichia coli* extract (ECE), wheat germ extract (WGE), rabbit reticulocytes lysate (RLL) and insect cell extract (ICE). These contain diverse cellular components and cofactors that enhance protein expression, folding and modification in different ways. Therefore, the most appropriate system will depend on the origin and the biochemical nature of the target protein. The preparation of ECE is simple and inexpensive, and generally achieves the highest protein yields, from hundreds of micrograms to milligrams per milliliter in batch reactions depending on the target protein.

In contrast, eukaryotic systems are less productive and extract preparation is more laborious, but complex proteins can be produced more efficiently and extended post-translational modifications are supported. WGE normally yields tens of micrograms to milligrams of recombinant protein per milliliter, depending on the protein and reaction format, but extract preparation takes 4-5 d, and the yield of extract from wheat seeds is low. The yields of RLL systems are typically two orders of magnitude lower than WGE and ICEs prepared from *Spodoptera frugiperda* can achieve yields of up to 50 µg/mL.

Recently two further eukaryotic systems based on CHO cells and *Saccharomyces cerevisiae* have been described. The CHO extract yields up to 50 µg/mL active firefly luciferase, but the fermentation medium is quite expensive. In contrast, the preparation of the yeast extract is inexpensive, but the system produces only low target protein levels of 8 µg/mL active firefly luciferase. The drawbacks of current cell-free systems have therefore created a demand for highly productive eukaryotic cell-free systems that can be prepared quickly in large amounts.

An uncoupled CFPS system based on tobacco BY-2 cells has been described in the literature (Buntru et al. Buntru et al. BMC Biotechnology 2014, 14:37). Furthermore, a highly efficient coupled cell-free transcription-translation system based on tobacco BY-2 cell lysates (BYLs) was also described in the prior art (Buntru et al, Biotechnology and Bioengineering, Vol. 112, No. 5, 2015, 867-878).

However, the prior cell-free protein synthesis systems have been limited in their wide uses and applications owing to their high cost for establishment. The problem of high cost comes from a complicated and cost-consuming procedure for preparing cell extracts which serve as a catalyst for cell-free protein synthesis. Furthermore, the preparation of the lysate or extract are often time consuming what makes it economical unfeasible to prepare it freshly for each in vitro translation reaction.

Therefore, it is an object of the present disclosure to provide improved methods and cell-free protein synthesis systems for in vitro protein synthesis not having the disadvantages of the prior art.

SUMMARY OF THE DISCLOSURE

The present disclosure relates generally to the field of cryopreservation of cell-free protein synthesis (also called in vitro protein synthesis or abbreviated CFPS). More specifically, the present disclosure relates to method and systems for treatment of eukaryotic cell lysates (or extracts) with so called cryoprotectants (e.g. sugars, DMSO, amino acids, compatible solutes) to maintain metabolic activity of the cell lysate during short- and long-term storage below freezing point.

In a first aspect, the present disclosure pertains to novel cell-free protein synthesis systems suitable for protein synthesis before and after freezing for a short- or long-term storage, wherein said system comprises a cryoprotectant.

In particular, the cryoprotectant is a non-reducing sugar trehalose or dimethyl sulfoxide (DMSO), in particular the concentrations of trehalose is in a range between 0.5 and 10% w/v, in particular between 1.0 and 5.0% w/v, in particular between 1.25 and 2.5% w/v, and the concentration of DMSO is in a range between 0.8 or 8%, in particular between 1 and 4% v/v.

The present disclosure pertains in a second aspect to further novel methods for cell-free protein synthesis, wherein said methods comprise the steps of:
a) Freezing a cell-free protein synthesis system according to the present disclosure to a temperature below −50° C., below −60° C., below −70° C. below −80° C., below −90° C. or below −196° C.,
b) storing said frozen cell-free protein synthesis system,
c) thawing said cell-free protein synthesis system,
d) synthesizing a protein in vitro by using said cell-free protein synthesis system and a nucleic acid template.

In a third aspect, the present disclosure relates to methods of preserving a cell-free protein synthesis system comprising the steps of:
a) Contacting a cell-free protein synthesis system with a cryoprotectant to obtain a cell-free protein synthesis system according to the present disclosure,
b) freezing said cell-free protein synthesis system in contact with said cryoprotectant.

BRIEF DESCRIPTION OF THE DRAWINGS

FIG. 1 is a diagram showing the yield of eYFP in coupled cell-free transcription-translation reactions using tobacco BY-2 cell lysate (BYL) before freezing and after freezing in liquid nitrogen and storage at −80° C. for one day.

DETAILED DESCRIPTION OF THIS DISCLOSURE

The present disclosure pertains to novel methods and systems for cell-free protein synthesis, in particular to cell-free protein synthesis systems suitable for protein synthesis before and after freezing for a short- or long-term storage, wherein said system comprises a cryoprotectant.

It is an advantage of the present that the cell-free translation systems according to the present disclosure can be frozen and stored before using. Therefore, a bulk of cell extracts/lysates can be produced, frozen and stored and do not need to be prepared freshly before used. Lysates derived from different prokaryotic and eukaryotic cells like yeast, mammalian or plant cells were established. Lysate or extract preparation methods are often time consuming what makes it economical unfeasible to prepare it freshly for each in vitro translation reaction. So storage and long-term stability for such lysate/extract preparations are of high interest.

The present disclosure describes the freezing of cell-free lysates in particular for long-term storage. In an advantageous embodiment, a recently developed cell-free system based on tobacco BY-2 cell lysate (BYL) (Buntru et al. BMC Biotechnology 2014, 14:37 and Buntru et al. Biotechnology and Bioengineering, Vol. 112, No. 5, 2015, 867-878) showed a high decrease in protein translational activity after freezing in liquid nitrogen, storage at −80° C. and thawing compared to freshly prepared lysate before freezing. To circumvent the problem of activity loss and maintain the lysate characteristics during cryostorage, the addition of certain cryoprotectants like DMSO, amino acids, and sugars like trehalose increase and maintain the in-vitro translation capability of the cell-free lysate after a freezing-thawing cycle.

As mentioned above, the present disclosure pertains to a cell-free protein synthesis system suitable for protein synthesis before and after freezing for a short- or long-term storage, wherein said system comprises a cryoprotectant.

Cell-free protein synthesis (also called in vitro protein synthesis or abbreviated CFPS), is the production of protein using biological machinery without the use of living cells. The in vitro protein synthesis environment is not constrained by a cell wall or homeostasis conditions necessary to maintain cell viability. Thus, CFPS enables direct access and control of the translation environment, which is advantageous for a number of applications including optimization of protein production, optimization of protein complexes, to study protein synthesis, incorporating non-natural amino acids, high-throughput screens, and synthetic biology.

Cell-free protein synthesis (CFPS)-systems have emerged as a powerful technology for protein expression. Prominent applications include the production of pharmaceutical proteins and vaccines (Goerke, A. R. et al. "Development of cell-free protein synthesis platforms for disulfide bonded proteins," Biotechnol. Bioeng. 99, 351-367 (2008); Kanter, G. et al. "Cell-free production of scFv fusion proteins: An efficient approach for personalized lymphoma vaccines," Blood 109, 3393-3399, (2007); Stech, M. et al. "Production of functional antibody fragments in a vesicle-based eukaryotic cell-free translation system," J. Biotechnol. 164, 220-231 (2012); Yang, J. et al. "Rapid expression of vaccine proteins for B-cell lymphoma in a cell-free system," Biotechnol. Bioeng. 89, 503-511 (2005); Yin, G. et al. "Aglycosylated antibodies and antibody fragments produced in a scalable in vitro transcription-translation system," MAbs 4, 217-225 (2012); Zawada, J. F. et al. "Microscale to manufacturing scale-up of cell-free cytokine production—a new approach for shortening protein production development timelines," Biotechnol. Bioeng. 108, 1570-1578 (2011)).

Such systems enable in vitro expression of proteins that are difficult to produce in vivo, as well as rapid and high-throughput production of protein libraries for protein evolution, functional genomics, and structural studies (Madin, K. et al. "A highly efficient and robust cell-free protein synthesis system prepared from wheat embryos: Plants apparently contain a suicide system directed at ribosomes," Proc. Natl. Acad. Sci. U.S.A. 97, 559-564 (2000); Takai, K et al. "Practical cell-free protein synthesis system using purified wheat embryos," Nat. Protoc. 5, 227-238 (2010)).

Two basic components are needed to accomplish in vitro protein expression: (1) the genetic template (mRNA or DNA) encoding the target protein and (2) a reaction solution containing the necessary transcriptional and translational molecular machinery. Cell extracts (or cell-free protein synthesis (CFPS) system) supply all or most of the molecules of the reaction solution, including:
RNA polymerases for mRNA transcription,
ribosomes for polypeptide translation,
tRNAs and amino acids,
enzymatic cofactors and an energy source,
cellular components essential for proper protein folding.

Cell lysates provide the correct composition and proportion of enzymes and building blocks required for translation (usually, an energy source and amino acids must also be added to sustain synthesis). Cell membranes are removed to leave only the cytosolic and organelle components of the cell (hence the term, "cell-free extracts/lysates"). The first types of lysates developed for cell-free protein expression were derived from prokaryotic organisms. More recently, systems based on extracts from insect cells, mammalian cells and human cells have been developed and made commercially available.

The cell-free protein synthesis systems according to the present disclosure comprise a biological extract/lysate like a prokaryotic or eukaryotic cellular lysate. The reaction mix for protein transcription/translation will comprise a template for production of the macromolecule, e.g. DNA, mRNA, etc.; monomers for the macromolecule to be synthesized, e.g. amino acids, nucleotides, etc., and such cofactors, enzymes and other reagents that are necessary for the synthesis, e.g. ribosomes, tRNA, polymerases, transcription factors, an energy regeneration system, e.g. creatine phosphate/creatine kinase, etc. Such synthetic reaction systems are well known in the art, and have been described in the literature. A number of reaction chemistries for polypeptide synthesis can be used in the methods of the invention. For example, reaction chemistries are described in U.S. Pat. No. 6,337,191, issued Jan. 8, 2002, and U.S. Pat. No. 6,168,931, issued Jan. 2, 2001.

Cell-free expression systems can support protein synthesis from DNA templates (transcription and translation) or mRNA templates (translation only). In principle, cell-free expression systems can be designed to accomplish transcription and translation steps as two separate sequential reactions (uncoupled) or concurrently as one reaction (coupled).

Prokaryotic *Escherichia coli* extract based cell-free systems have developed rapidly (for a review, see Carlson, E. D. et al. "Cell-free protein synthesis: Applications come of age," Biotechnol. Adv. 30, 1185-1194, (2012)). For purposes of the invention, any prokaryotic or eukaryotic cellular lysate can be used as a cell-free protein synthesis system. As a prokaryotic cellular lysate as a cell-free protein synthesis system, *E. coli* S30 cell-free extracts were described by Zubay, G. (1973, Ann. Rev. Genet. Vol 7, p. 267). These can be used when the gene to be expressed has been cloned into a vector containing the appropriate prokaryotic regulatory sequences, such as a promoter and ribosome-binding site.

Cell-free systems are considered "coupled" if the transcription and translation occur simultaneously after the addition of DNA to the extract. In some advantageous embodiment, the cell-free protein synthesis system according to the present disclosure is a coupled cell-free protein synthesis system.

However, eukaryotic cell-free lysates are preferred expression systems for many reasons, at least partially because they retain a variety of post-translational processing activities. For example, with the addition of canine microsomal membranes to cell-free wheat germ extract processing events, such as signal peptide cleavage and core glycosylation, can be examined. Eukaryotic cellular lysates also support the translation in vitro of a wide variety of viral and other prokaryotic RNAs, as well as eukaryotic mRNAs.

The major eukaryotic CFPS platforms previously developed include systems made from wheat germ extract (WGE) (Goshima, N. et al. "Human protein factory for converting the transcriptome into an in vitro-expressed proteome," Nat. Methods 5, 1011-1017 (2008); Hoffmann, M. et al. in Biotechnol Annu Rev Vol. 10, 1-30 (Elsevier, 2004); Takai et al. (2010)), rabbit reticulocyte lysate (RRL) (Jackson, R. J. et al. in Methods Enzymol Vol. Vol. 96 (eds. Becca Fleischer, Sidney Fleischer) Ch. 4, 50-74 (Academic Press, 1983)); insect cell extract (ICE) (Ezure, T et al. "A cell-free protein synthesis system from insect cells," Methods Mol. Biol. 607, 31-42 (2010); Kubick, S et al. in Current Topics in Membranes, Vol. 63 (ed. Larry DeLucas) 25-49 (Academic Press, 2009); Tarui, H. et al. "Establishment and characterization of cell-free translation/glycosylation in insect cell (*Spodoptera frugiperda* 21) extract prepared with high pressure treatment," Appl. Microbiol. Biotechnol. 55, 446-453 (2001)); *Leishmania tarentolae* extract (Kovtun, O. et al. "Towards the construction of expressed proteomes using a *Leishmania tarentolae* based cell-free expression system," PLoS One 5, e14388 (2010); Mureev, S. et al. "Species-independent translational leaders facilitate cell-free expression," Nat. Biotechnol. 27, 747-752 (2009)); and HeLa and hybridoma cell extract (Mikami, S. et al. in Cell-Free Protein Production Vol. 607 Methods in Molecular Biology (eds. Yaeta Endo, Kazuyuki Takai, & Takuya Ueda) Ch. 5, 43-52 (Humana Press, 2010)). All these eukaryotic lysates are popular with researchers, and are widely available.

According to the present disclosure, cell extracts used as a cell-free protein synthesis system may be prepared by methods comprising the sequential steps of cell lysis, high-speed centrifugation (30,000 RCF), pre-incubation, dialysis and low-speed centrifugation (4,000 RCF). The cells used in the present disclosure are preferably selected from the group consisting of *E. coli, Bacillus subtilis*, wheat germ, rice germ, barley germ, CHO cells, hybridoma cells and reticulocytes, but not limited thereto.

In an advantageous embodiment of the present disclosure, tobacco BY-2 cell lysates are preferred. This tobacco BY-2 cell lysate could be prepared e.g. by a method described by Buntru et al. BMC Biotechnology 2014, 14:37 and Buntru et al. Biotechnology and Bioengineering, Vol. 112, No. 5, 2015, 867-878 (see examples).

The cell-free protein synthesis system according to the present disclosure comprises a cryoprotectant. A cryoprotectant is an antifreeze compound or antifreeze protein (AFP) used to stabilize proteins and membranes against freezing-induced stress (i.e. due to ice formation). Cryoprotectants are chemicals that reduce damage associated with cryopreservation. Examples of cryoprotectants are amino acids or derivatives thereof, sugars like di- or oligosaccharides or derivatives thereof, sarcosine, proline, betaine, ectoine, hydroxyectoine, N-acetyl lysine, glycosylglycerate, as well as ethylenglycol, polyvinylpyrrolidone, PEG or mixtures thereof.

A cryoprotectant comprised in a cell-free protein synthesis system according to the present disclosure may be selected from the group consisting of acetamide, agarose, alginate, alanine, albumin, ammonium acetate, anti-freeze proteins, betaine, butanediol, chondroitin sulfate, chloroform, choline, cyclohexanediols, cyclohexanediones, cyclohexanetriols, dextrans, diethylene glycol, dimethyl acetamide, dimethyl formamide, dimethyl sulfoxide, erythritol, ethanol, ethylene glycol, ethylene glycol monomethyl ether, formamide, glucose, glycerol, glycerophosphate, glyceryl monoacetate, glycine, glycoproteins, hydroxyethyl starch, inositol, lactose, magnesium chloride, magnesium sulfate, maltose, mannitol, mannose, methanol, methoxy propanediol, methyl acetamide, methyl formamide, methyl ureas, methyl glucose, methyl glycerol, phenol, pluronic polyols, polyethylene glycol, polyvinylpyrrolidone, proline, propanediol, pyridine N-oxide, raffinose, ribose, serine, sodium bromide, sodium chloride, sodium iodide, sodium nitrate, sodium nitrite, sodium sulfate, sorbitol, sucrose, trehalose, triethylene glycol, trimethylamine acetate, urea, valine, xylose and mixtures thereof.

In some advantageous embodiments, the cryoprotectant comprised in the cell-free protein synthesis system according to the present disclosure is a non-reducing sugar like trehalose and/or a dimethyl sulfoxide (DMSO). In some advantageous embodiments, the concentration of trehalose is surprisingly in a low concentration range between 0.5 and 10% w/v, in particular in a range between 1 and 5% w/v, in particular between 1.25 and 2.5% w/v. When using DMSO as the cryoprotectant the concentrations of DMSO is in a range between 0.8 or 8%, in particular between 1 and 4% v/v.

In a preferred embodiment, the cryoprotectant is trehalose or DMSO. After freezing and thawing procedure the lysates with added cryoprotectants show up to 21 fold higher translational activity and keep around 100% of the activity of a freshly prepared lysate before freezing (FIG. 1).

Therefore, the addition of cryoprotective substances to freshly prepared eukaryotic cell lysate, in particular to tobacco BY-2-lysate are essential to keep lysate functionality after cryostorage and thawing. This is especially important when functional organelles of the lysate like microsomes, and other vesicular structures are needed.

In an advantageous embodiment of the present disclosure, a cell-free system based on tobacco BY-2 cell lysate (BYL) (Buntru et al., 2014; 2015) showed a high decrease in protein translational activity after freezing at −80° C. and thawing compared to freshly prepared lysate before freezing. To circumvent the problem of activity loss and maintain the lysate characteristics during cryostorage we figured out that by addition of certain cryoprotectants like DMSO, amino acids, and sugars preferable trehalose we can increase and maintain the in vitro translation capability of the cell-free lysate after a freezing-thawing cycle.

Compounds in addition to trehalose that should be also useful for the cryopreservation of the BYL include other sugars and combinations of sugars; other metabolic activators and inhibitors; and other impermeable protective or compatible osmolytes such as di- or oligosaccharides, sarcosine, proline, betaine, ectoine, hydroxyectoine, N-acetyl lysine, glycosylglycerate, as well as ethylenglycol, polyvinylpyrrolidone, PEG and derivatives. Trehalose is a preferred cryoprotectant because it is a non-reducing sugar, meaning that it does not readily react with the amine groups of proteins, which can be harmful.

In advantageous embodiments, the cell-free protein synthesis system according to the present disclosure is frozen (not freeze-dried), i.e. the cell-free protein synthesis system has a temperature below −50° C., below −60° C., below −70° C. below −80° C., below −90° C. or below −196° C.

Furthermore, the present disclosure pertains to methods for cell-free protein synthesis according to the present disclosure comprises the steps of:
a) Freezing the cell-free protein synthesis system according to the present disclosure to a temperature below −50° C., below −60° C., below −70° C. below −80° C., below −90° C. or below −196° C.,
b) storing said frozen cell-free protein synthesis system,
c) thawing said cell-free protein synthesis system,
d) synthesizing a protein in vitro by using said cell-free protein synthesis system and a nucleic acid template.

As mentioned above, the cell-free protein synthesis system according to the present disclosure is frozen, i.e. the cell-free protein synthesis system has a temperature below −50° C., below −60° C., below −70° C. below −80° C., below −90° C. or below −196° C.

Methods for freezing the cell-free protein synthesis system include shock freezing of freshly prepared and aliquoted lysate preparations by immerging the lysate aliquots (in polypropylene tubes) in liquid nitrogen at −196° C. for 5 min and afterwards storage at either −80° C. or under liquid nitrogen at −196° C. Alternatively, the freshly prepared and aliquoted lysate preparations can be directly stored at −80° C.

Furthermore, the method according to the present disclosure comprises storing the cell extracts for cell-free protein synthesis at a temperature between −20 to −196° C. or below. This could be a short-term storage or preferably a long-term storage over several days, weeks, month or years.

Surprisingly, the inventors found that it is not necessary to remove the cryoprotectant before synthesizing a protein using the cell-free protein synthesis system according to the present disclosure.

In advantageous embodiments, the cell-free protein synthesis system is thawed at room temperature before usage (i.e. synthesize a protein). Preferably, the synthesizing step (d) is carried out at a temperature between 20 and 25° C.

As used herein, "expression template" or "nucleic acid template" refer to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template", "nucleic acid template" refer and "transcription template" have the same meaning and are used interchangeably.

As used herein, "translation template" refers to an RNA product of transcription from an expression template that can be used by ribosomes to synthesize polypeptide or protein. The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N-glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

In some advantageous embodiments, in the methods according to the present disclosure the protein synthetization is realized in the presents of a reaction mixture, in particular in a CFPS reaction mixture. The term "reaction mixture" as used herein, refers to a solution containing reagents necessary to carry out a given reaction. A "CFPS reaction mixture" typically contains a crude or partially purified prokaryotic or eukaryotic cellular extract/lysate, a DNA transcription template (or RNA translation template), and a suitable reaction buffer for promoting cell-free protein synthesis from the DNA transcription template (or RNA translation template). In some embodiments, the CFPS reaction mixture can include exogenous RNA translation template. In other embodiments, the CFPS reaction mixture can include a DNA expression template encoding an open reading frame operably linked to a promoter element for a DNA-dependent RNA polymerase. In these other aspects, the CFPS reaction mixture can also include a DNA-dependent RNA polymerase to direct transcription of an RNA translation template encoding the open reading frame. In these other aspects, additional NTP's and divalent cation cofactor can be included in the CFPS reaction mixture. A reaction mixture is referred to as complete if it contains all reagents necessary to enable the reaction, and incomplete if it contains only a subset of the necessary reagents.

It will be understood by one of ordinary skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of ordinary skill in the art that reaction components are packaged separately for commercialization and that useful commercial kits may contain any subset of the reaction components of the invention.

A typical set-up for synthesizing a protein in vitro by using said cell-free protein synthesis system is described below. A lysate aliquot is taken from −80° C. storage and thawed at room temperature. To start protein expression, a nucleic acid template is added to the lysate—DNA in case of a coupled transcription-translation reaction and mRNA in case of an uncoupled transcription-translation reaction—plus a reaction mixture composed of HEPES buffer, magnesium glutamate, potassium glutamate, NTP's (ATP, GTP, CTP and UTP for coupled transcription-translation reactions, ATP and GTP for uncoupled transcription-translation reactions), creatine phosphate, creatine kinase, and T7 RNA polymerase (only for coupled transcription-translation reactions). Both coupled and uncoupled transcription-translation reactions are carried out at 25° C. and 700 rpm for 18 h in a thermomixer. Based on the nature of the target protein the synthesized protein can be analyzed by different methods, e.g. fluorescence measurement, enzymatic assay, and SDS PAGE.

Further embodiments of the present disclosure pertains to methods of preserving a cell-free protein synthesis system comprising the steps of:
a) Preparing a cell-free protein synthesis system with a cryoprotectant to obtain a cell-free protein synthesis system according to the present disclosure,
b) freezing said cell-free protein synthesis system in contact with said cryoprotectant.

EXAMPLES

In one embodiment of the present disclosure a BYL as described in Buntru et al. (2015) was prepared.
Preparation of the Tobacco BY-2 Lysate (BYL)
The preparation of lysate from evacuolated BY-2 protoplasts was carried out as described by Komoda et al. (2004) and Gursinsky et al. (2009) with significant modifications. Protoplasts were prepared from cells in the exponential growth phase of a continuous fermentation by treating the cells with 3.5% (v/v) Rohament CL, and 0.2% (v/v) Rohapect UF (both from AB Enzymes, Darmstadt, Germany) directly in the fermentation medium. The osmolarity of the medium was adjusted by addition of 360 mM mannitol. The resulting protoplasts were layered onto a discontinuous Percoll gradient containing (from bottom to top) 70% (v/v, 3 ml), 40% (v/v, 5 ml), 30% (v/v, 3 ml), 15% (v/v, 3 ml) and 0% (3 ml) Percoll (GE Healthcare, Munich, Germany) in 0.7 M mannitol, 20 mM $MgCl_2$, and 5 mM PIPES-KOH (pH 7.0). After centrifugation at 6,800 g for 1 h at 25° C. in a swinging bucket rotor, evacuolated protoplasts were recovered from the 40-70% (v/v) Percoll solution interface. The evacuolated protoplasts were suspended in three volumes of TR buffer (30 mM HEPES-KOH (pH 7.4), 60 mM potassium glutamate, 0.5 mM magnesium glutamate, 2 mM DTT) supplemented with one tablet per 50 ml of Complete EDTA-free Protease Inhibitor Mixture (Roche Diagnostics, Mannheim, Germany) and disrupted using 30 strokes with a Dounce tissue grinder (Sigma-Aldrich, St. Louis, Mo., USA). Nuclei and non-disrupted cells were removed by centrifugation at 500 g for 10 min at 4° C.

Different amounts of cryoprotective compounds were added to aliquots of the supernatant like trehalose in concentrations of 1.25%, 2.5% and 5%, DMSO in concentrations of 1%, 2% and 4% as well as the amino acid proline in the concentration of 0.5%.

Some of these freshly prepared aliquots were directly used in coupled in vitro transcription-translation reactions with a plasmid template encoding for the fluorescent reporter protein eYFP (Buntru et al., 2015). The remaining aliquots were shock frozen in liquid nitrogen and stored at −80° C. After one day of storage at −80° C. the aliquots were thawed at room temperature to repeat the coupled in vitro transcription-translation reactions under same conditions as mentioned before.
In Vitro Translation Activity of BYL in Batch Reactions The performance of the BYL was investigated by producing the reporter protein eYFP using the plasmid pIVEX_GAAAGA_Omega_Strep-eYFP as the template. Coupled transcription-translation reactions were performed in 50 µl aliquots at 25° C. and 500 rpm for 16 h in an incubator shaker (Kuehner, Basel, Switzerland). Standard reactions contained 40% (v/v) BYL, 40 mM HEPES-KOH (pH 7.8), 8.5 mM magnesium glutamate, 3 mM ATP, 1.2 mM GTP, 1.2 mM CTP, 1.2 mM UTP, 30 mM creatine phosphate, 0.1 µg/µL creatine kinase, 80 ng/µl vector DNA, and 50 ng/µl homemade T7 RNA polymerase.

The fluorescence signal from eYFP was quantified using a Synergy HT Multi-Mode Microplate Reader (Biotek, Bad Friedrichshall, Germany) with 485/20 nm excitation and 528/20 nm emission filters. The quantity of eYFP was determined by generating a standard curve based on different concentrations of eYFP in BYL transcription-translation reactions without a DNA template. The eYFP standard was produced using the BYL transcription-translation system and purified by Strep-Tactin® Sepharose®. The concentration of purified eYFP was determined using a colorimetric assay (Bradford, 1976).
Results After freezing and thawing procedure the lysates with added cryoprotectants show up to 21 fold higher translational activity and keep around 100% of the activity of a freshly prepared lysate before freezing (FIG. 1).

FIG. 1 shows the yield of eYFP in coupled cell-free transcription-translation reactions using tobacco BY-2 cell lysate (BYL) before freezing and after shock freezing in liquid nitrogen and storage at −80° C. for one day. Aliquots of the lysate were supplemented with different amounts of the cryoprotectants (CP) trehalose, DMSO and proline. Using plasmid pIVEX_GAAAGA_Omega_Strep-eYFP as a template reactions were performed at 25° C. and 500 rpm for 16 h. The fluorescent signal from eYFP was quantified using a fluorescence reader with 485/20 nm excitation and 528/20 nm emission filters. The quantity of eYFP was determined by generating a standard curve based on different concentrations of eYFP in BYL transcription-translation reactions without a DNA template. The eYFP standard was produced using the BYL transcription-translation system and purified by Strep-Tactin® Sepharose®. The concentration of purified eYFP was determined using a colorimetric assay. Data represent the averages and standard deviations of three independent transcription-translation experiments.

LITERATURE

Bradford M M. 1976. A rapid and sensitive method for the quantitation of microgram quantities of protein utilizing the principle of protein-dye binding. Anal Biochem 72:248-54.
Buntru M, Vogel S, Spiegel H, Schillberg S. 2014. Tobacco BY-2 cell-free lysate: an alternative and highly-productive plant-based in vitro translation system. BMC Biotechnol. 14: 37. doi:10.1186/1472-6750-14-37.
Buntru M, Vogel S, Stoff K, Spiegel H, Schillberg S. 2015. A Versatile Coupled Cell-Free Transcription-Translation System Based on Tobacco BY-2 Cell Lysate. Biotechnol. Bioeng. 112(5):867-78. doi: 10.1002/bit.25502.
Gursinsky T, Schulz B, Behrens S E. 2009. Replication of Tomato bushy stunt virus RNA in a plant in vitro system. Virology 390(2):250-60.
Hodgman C E, Jewett M C. 2013. Optimized extract preparation methods and reaction conditions for improved yeast cell-free protein synthesis. Biotechnol Bioeng 110(10): 2643-54.
Komoda K, Naito S, Ishikawa M. 2004. Replication of plant RNA virus genomes in a cell-free extract of evacuolated plant protoplasts. Proc Natl Acad Sci USA 101(7):1863-1867.

What is claimed is:

1. A cell-free protein synthesis system suitable for protein synthesis before and after freezing for a short- or long-term storage, wherein said system comprises a cryoprotectant, wherein said cell-free protein synthesis system is a tobacco BY-2 cell lysate, wherein said cryoprotectant is trehalose or dimethyl sulfoxide (DMSO), wherein a concentration of trehalose is in a range between 1.25 and 2.5% w/v and a concentration of DMSO is in a range between 1 and 4% v/v.

2. The cell-free protein synthesis system according to claim 1, wherein said cell-free protein synthesis system is frozen.

3. The cell-free protein synthesis system according to claim 1, wherein said cell-free protein synthesis system is stored at a temperature below −50° C., below −60° C., below −70° C., below −80° C., below −90° C. or below −196° C.

4. A method for cell-free protein synthesis, said method comprising the steps of:
a) freezing the cell-free protein synthesis system according to claim 1 to a temperature below −50° C., below −60° C., below −70° C., below −80° C., below −90° C. or below −196° C.;
b) storing said frozen cell-free protein synthesis system;
c) thawing said cell-free protein synthesis system; and
d) synthesizing a protein in vitro by using said cell-free protein synthesis system and a nucleic acid template.

5. The method according to claim 4, wherein the cryoprotectant is not removed before synthesizing a protein.

6. The method according to claim 4, wherein the cell-free protein synthesis system is thawed at room temperature before usage.

7. A method of preserving a cell-free protein synthesis system comprising the steps of:
a) contacting a cell-free protein synthesis system with a cryoprotectant to obtain a cell-free protein synthesis system according to claim 1; and
b) freezing said cell-free protein synthesis system in contact with said cryoprotectant.

8. The method according to claim 7, wherein said cell-free protein synthesis system is frozen by shock freezing.

9. The method according to claim 7, wherein said cell-free protein synthesis system is frozen to a temperature below −50° C., below −60° C., below −70° C., below −80° C., below −90° C. or below −196° C.

10. The method according to claim 7, wherein the frozen cell-free protein synthesis system is thawed at room temperature before usage.

* * * * *